United States Patent
Hochi et al.

(10) Patent No.: US 9,420,838 B2
(45) Date of Patent: Aug. 23, 2016

(54) ALL-PURPOSE WIG, METHOD FOR FITTING WIG, AND CUSTOMIZED WIG

(75) Inventors: Hiroshi Hochi, Tokyo (JP); Kenichiro Kanno, Saitama (JP)

(73) Assignee: PROPIA CO., LTD., Tokyo (JP)

( * ) Notice: Subject to any disclaimer, the term of this patent is extended or adjusted under 35 U.S.C. 154(b) by 885 days.

(21) Appl. No.: 13/522,555

(22) PCT Filed: Jan. 13, 2011

(86) PCT No.: PCT/JP2011/050428
§ 371 (c)(1),
(2), (4) Date: Jul. 17, 2012

(87) PCT Pub. No.: WO2011/089962
PCT Pub. Date: Jul. 28, 2011

(65) Prior Publication Data
US 2013/0014776 A1 Jan. 17, 2013

(30) Foreign Application Priority Data

Jan. 19, 2010 (JP) ................................. 2010-009413

(51) Int. Cl.
*A41G 3/00* (2006.01)
*A61F 2/10* (2006.01)

(52) U.S. Cl.
CPC ................ *A41G 3/0025* (2013.01); *A61F 2/10* (2013.01)

(58) Field of Classification Search
CPC ....... A41G 5/0033; A41G 5/008; A41G 5/00; A41G 5/0013; A41G 5/0026; A41G 5/0006; A41G 3/0025; A41G 3/0066; A41G 3/0033; A41G 3/0016; A41G 3/00; A41G 3/0041; A41G 3/005; A41G 3/0008; A41G 3/0058; A41G 3/0091
See application file for complete search history.

(56) References Cited

U.S. PATENT DOCUMENTS 2,850,023 A * 9/1958 Taylor .................. A41G 5/0033
132/53
4,453,555 A * 6/1984 Finamore ................. A41G 3/00
132/201

(Continued)

FOREIGN PATENT DOCUMENTS

AU 2004277820 B2 4/2005
CA 2 540 046 A1 4/2005

(Continued)

OTHER PUBLICATIONS

Chinese Office Action dated Jan. 26, 2014 (and English translation thereof) in counterpart Chinese Application No. 201180006510.4.

(Continued)

*Primary Examiner* — Todd E Manahan
*Assistant Examiner* — Brianne Kalach
(74) *Attorney, Agent, or Firm* — Holtz, Holtz & Volek PC

(57) ABSTRACT

An all-purpose wig has a base including an ultrathin and moisture permeable film-shaped material, and hair materials adhered to one surface of the base. A first adhesion layer includes an adhesion agent having comparatively strong adhesion and a comparatively large degree of gelling. A second adhesion layer includes an adhesion agent having comparatively weak adhesion and a comparatively small degree of gelling. The first adhesion layer and the second adhesion layer are provided adjacent to each other with a tank layer therebetween. A first release layer is attached peelably to the whole surface of the second adhesion layer on the side that is fit to the skin, and a second release layer is applied peelably to the first adhesion layer and is layered on a portion of the surface between the first adhesion layer and the tank layer. The layers are layered in order, forming a flat surface.

12 Claims, 22 Drawing Sheets

(56) References Cited

U.S. PATENT DOCUMENTS

| | | |
|---|---|---|
| 7,784,472 B2 | 8/2010 | Hochi |
| 7,909,041 B2 | 3/2011 | Yoneda et al. |
| 2007/0119468 A1 | 5/2007 | Hochi |
| 2009/0126753 A1 | 5/2009 | Sugai et al. |

FOREIGN PATENT DOCUMENTS

| | | | |
|---|---|---|---|
| CN | 1758860 A | | 4/2006 |
| CN | 101065030 A | | 10/2007 |
| EP | 1 671 557 A1 | | 6/2006 |
| JP | 2001-089921 A | | 4/2001 |
| JP | 2005-113300 A | | 4/2005 |
| JP | 4009910 B2 | | 9/2007 |
| RU | 2 339 283 C2 | | 11/2008 |
| WO | WO01/00116 | * | 1/2001 |
| WO | WO 2005/032291 A1 | | 4/2005 |

OTHER PUBLICATIONS

International Search Report dated Feb. 15, 2011 issued in International Appln. No. PCT/JP2011/050428.

Supplementary European Search Report dated Jul. 3, 2013 (in English) in counterpart European Application No. 11 734 569.4.

European Office Action dated Nov. 13, 2015, issued in counterpart European Application No. 11734569.4.

International Preliminary Report on Patentability (IPRP) and Written Opinion dated Aug. 7, 2012 (and English translation thereof) in parent International Application No. PCT/JP2011/050428.

* cited by examiner (A)

(B)

(C)

(D)

(A)

(B)

ALL-PURPOSE WIG, METHOD FOR FITTING WIG, AND CUSTOMIZED WIG

This application is a U.S. National Phase Application under 35 USC 371 of international Application PCT/JP2011/050428 filed Jan. 13, 2011.

TECHNICAL FIELD

The present invention relates to a field of a wig, and specifically to an all-purpose wig, a method for fitting a wig and a customized wig.

BACKGROUND ART

A wig, especially one to be fitted on a head will be used everyday and, therefore, will deteriorate with time.

Because a popular wig that is manufactured by manual implantation has a very high price of hundreds of thousands of yen, it would in most cases be kept using, even if it has somewhat deteriorated with time such as having been color-faded and weakened. The deteriorated wig would be more easily found out, which should give more reluctance to wearing the wig, for a user who may even feel an inferior complex to wearing a wig, As a consequence, a disposable wig that has been proposed and produced on a commercial basis after many years' labor wins popularity not only in our country but also in foreign countries.

An example of this disposable type wig is disclosed in Japanese Patent No. 4009910. A wig 30 according to Patent Document 1 has a structure such as shown in FIG. 20(A), wherein a root portion 35 of a hair material 31 greatly juts out from one side of an ultra-thin base 33, the inside of the root portion 35 is secured to the base 33 by means of an adhesive 34 comprising a UV curing agent filled therebetween, which is covered by a sticky layer 37.

The sticky layer 37 comprises a sticky agent having properties of relatively strong adhesion and hardness, which will be prevented from accidental removal when being fitted to the skin.

Furthermore, as shown in FIG. 20(B), the structure is such that the concaves 38 and the convexes 39 formed between the root portions 35 and other portions will turn reversal with each other, when fitted to the skin 20, in order to prevent shining of the base due to irregular light reflection such as shown by arrows and also to prevent removal of the hair materials due to pressure F toward the base. However, this should result in the fact that the sticky layer is bonded to the skin 20 exactly only at the spots S (see FIG. 18). Although it is shown in FIG. 20(B) that the sticky layer 37 appears to have planar contact with the skin 20, the sticky layer 37 is bonded to the skin 20 at points S, because the skin 20 has slight unevenness in a microscopic viewpoint, as shown in FIG. 18.

Furthermore, when removed after being fitted, as shown in FIG. 21, a considerable number of stratum corneum 21 should be separated from the skin 20, because of strong adhesive force.

To prevent removal of the stratum corneum 21, it would be effective to use a sticky agent having relatively weak adhesion (herein later referred to by "weak sticking agent"), and the present inventors have tried to do so. However, it has been proved that this cannot solve the problem, because when the weak sticking agent is laid upon a sticky agent having relatively strong adhesion (hereinlater referred to by "strong sticking agent"), the adhesion of the weak sticking agent becomes stronger.

With respect to the spotty bonding, it is expected to solve this problem by creating the planar bonding to the skin 20. In order to achieve the planar bonding, hopefully, there is a relatively thick layer to be interposed between first and second sticky layers so as to absorb the protrusion of the root portions. However, when the interposed layer becomes thicker, the overall thickness of the wig also becomes greater, so that the receding hairline looks like a wig indeed, which provides a disadvantage of extremely decreasing the appearance.

Moreover, in a case of the strong sticky agent, there is a disadvantage that it is substantially impossible to eliminate the stratum corneum 21 adhered to the sticking surface of the sticking layer that has been separated.

Furthermore, in a wig using the strong sticky agent, there is a risk that the said strong sticky agent could remain on the skin 20. In addition, when the wig is fitted by a user him- or herself, the base tends to shrink due to strong sticky force of the sticky agent, which will in some case make it difficult to fit the wig well onto a desired site.

As described above, the wig has a restriction due to product thickness and, therefore, has inconsistent relationship between the sticky force and the planar bonding.

PRIOR ARTS

Patent Documents

Patent Document 1: JP4009910(B)

SUMMARY OF INVENTION

Problems to be Solved

In the above-described background, the present invention has a purpose to provide a two-dimensional all-purpose wig, a method for fitting the wig and a customized wig having just-fit property that enable planar bonding to the skin regardless of if a weak bonding agent is used, which enables reliable fitting and enables just-fit fitting to the head once customized to a shape of a head of a particular user.

Another purpose is to provide an all-purpose wig, a method for fitting the wig and a customized wig having just-fittability, said wig being wearable more definitely and more speedily.

Means for Solving the Problems

To achieve the above-described purposes, an all-purpose wig according to the present invention comprises a base, hair materials implanted to the base, a first adhesive layer formed on an entire surface of the base at a side of root portions of said hair materials, a tank layer, a second adhesive layer to be bonded to a skin, a first release layer and a second release layer, wherein said base comprises an ultra-thin and moisture permeable film-shaped material, the hair materials are implanted such that their root portions that form the implanting base end are adhered closely to one surface of said base, with their free end portions being oriented toward the other surface of said base, said first adhesive layer comprises an adhesive agent having the properties of relatively strong adhesion and relatively large degree of gelling, said second adhesive layer comprises an adhesive agent having the properties of relatively weak adhesion and relatively small degree of gelling, said tank layer comprises the same film-shaped material as said base, said first adhesive layer and said second adhesive layer are provided adjacent to each other with said tank layer therebetween, said first release layer is applied peelably to the entire surface of said second adhesive layer on a side that is fit to the skin, said second release layer is layered partially between said first adhesive layer and said tank layer and applied peelably to said first adhesive layer, and said wig is formed as a substantially two-dimensional, multi-layer structure wherein said base, said first adhesive layer, said second release layer, said tank layer, said second adhesive layer and said first release layer are laminated in this order.

In one embodiment, in the all-purpose wig according to Claim 1, said second release layer is formed at a latter half of said first adhesive layer.

In another embodiment, in the all-purpose wig according to Claim 1 or 2, said hair materials are implanted onto said base while their free end portions are in stretched condition.

In another embodiment, in the all-purpose wig according to Claim 1, the adhesion of said first adhesive layer is on the order of five times of the adhesion of said second adhesive layer.

In another embodiment, in the all-purpose wig according to Claim 1, said hair materials are randomly implanted onto said base.

A method for fitting a wig according to the present invention comprises a step of applying a second adhesive layer onto a corresponding site of a head, said second adhesive layer having been exposed by peeling a first release layer at a portion corresponding to a portion at which a second release layer is layered (hereinlater referred to by "layering portion"; a step of peeling a remaining portion of the first release layer so that a portion other than the layering portion of the second adhesive layer is applied onto the head; a step of applying first wrinkles to the second adhesive layer at a portion corresponding to said layering portion; a step of bonding the first-wrinkled portion to adjacent portions of the second adhesive layer; a step of peeling the second release layer to expose the layering portion of the first adhesive layer; a step of applying second wrinkles while the entire portion of said second adhesive layer is applied to the head; a step of applying said first adhesive layer onto a tank layer while in the second-wrinkled condition; and a step of cutting said second-wrinkled portion adjacent at their roots.

A customized wig according to the present invention comprises a base, hair materials implanted to the base, a first adhesive layer formed on an entire surface of the base at a side of root portions of said hair materials, a tank layer, a second adhesive layer to be bonded to a skin, a first release layer and a second release layer, wherein said base comprises an ultra-thin and moisture permeable film-shaped material, said hair materials are implanted such that their root portions that form the implanting base end are adhered closely to one surface of said base, with their free end portions being oriented toward the other surface of said base, said first adhesive layer comprises an adhesive agent having the properties of relatively strong adhesion and relatively large degree of gelling, said second adhesive layer comprises an adhesive agent having the properties of relatively weak adhesion and relatively small degree of gelling, said tank layer comprises the same film-shaped material as said base, said first adhesive layer and said second adhesive layer are provided adjacent to each other with said tank layer therebetween, said first release layer is applied peelably to the entire surface of said second adhesive layer on a side that is fit to the skin, said second release layer is layered partially between said first adhesive layer and said tank layer and applied peelably to said first adhesive layer, and said customized wig is formed as a substantially three-dimensional, multi-layer structure comprising said base, said first adhesive layer, said second release layer, said tank layer, said second adhesive layer and said first release layer are laminated in this order, wherein said tank layer is given first wrinkles by a first wrinkling step, said first wrinkles being bonded to adjacent portions, and said first adhesive layer is given second wrinkles by a second wrinkling step, said second wrinkles being cut adjacent at their roots.

In one embodiment, in the customized wig according to Claim 7, said second release layer is formed at a latter half of said first adhesive layer.

In another embodiment, in the customized wig according to Claim 7 or 8, said hair materials are implanted onto said base while their free end portions are in stretched condition.

In another embodiment, in the customized wig according to Claim 7, the adhesion of said first adhesive layer is on the order of five times of the adhesion of said second adhesive layer.

In another embodiment, in the customized wig according to Claim 7, said hair materials are randomly implanted onto said base.

Effects of Invention

Once the wig according to the present invention is customized to a shape of a head of a specific user, it is fitted to the head not only by means of adhesion of the second adhesive layer, but also due to the multi-layer structure that can be fitted around the head, said physical power being also contributed to fitting. Accordingly, even if the second adhesive layer has relatively weak adhesion, and even if there are some downy hairs, it can be securely fitted and will prevent accidental removal.

The wrinkling for customizing the wig to a shape of a head of a specific user is carried out in separate first and second steps, which makes it possible to carry out the customizing operation more accurately and more speedily, due to simplification of the operation.

The wrinkling is carried out in separate first and second steps, wherein the second-wrinkled portion is cut (by the cutting step), by which the surface of the multi-layer structure has no protrusion of unnecessary portions. Accordingly, the base film is prevented from twisting, which may otherwise appear due to the wrinkling, thereby providing an extremely favorable light permeability to the base. As a result, it becomes difficult to distinguish between the human skin and the film base, which provides more natural appearance and feeling. Because the surface of the multi-layer structure has no protrusion of unnecessary portions, the orientation of the hair materials is not disturbed by wrinkles and remains unchanged and constant, which will further improve the appearance.

The wig that has been customized is very easily fittable, because it can be done while visually confirming the plane to be bonded to the skin.

In accordance with a wig according to the present invention, an all-purpose wig having a two-dimensional configuration that is conformable to any user is manufactured in advance, which may be individually customized to a head shape of a specific user, even in a day.

EMBODIMENTS FOR PRACTICING THE INVENTION

Figure 1:
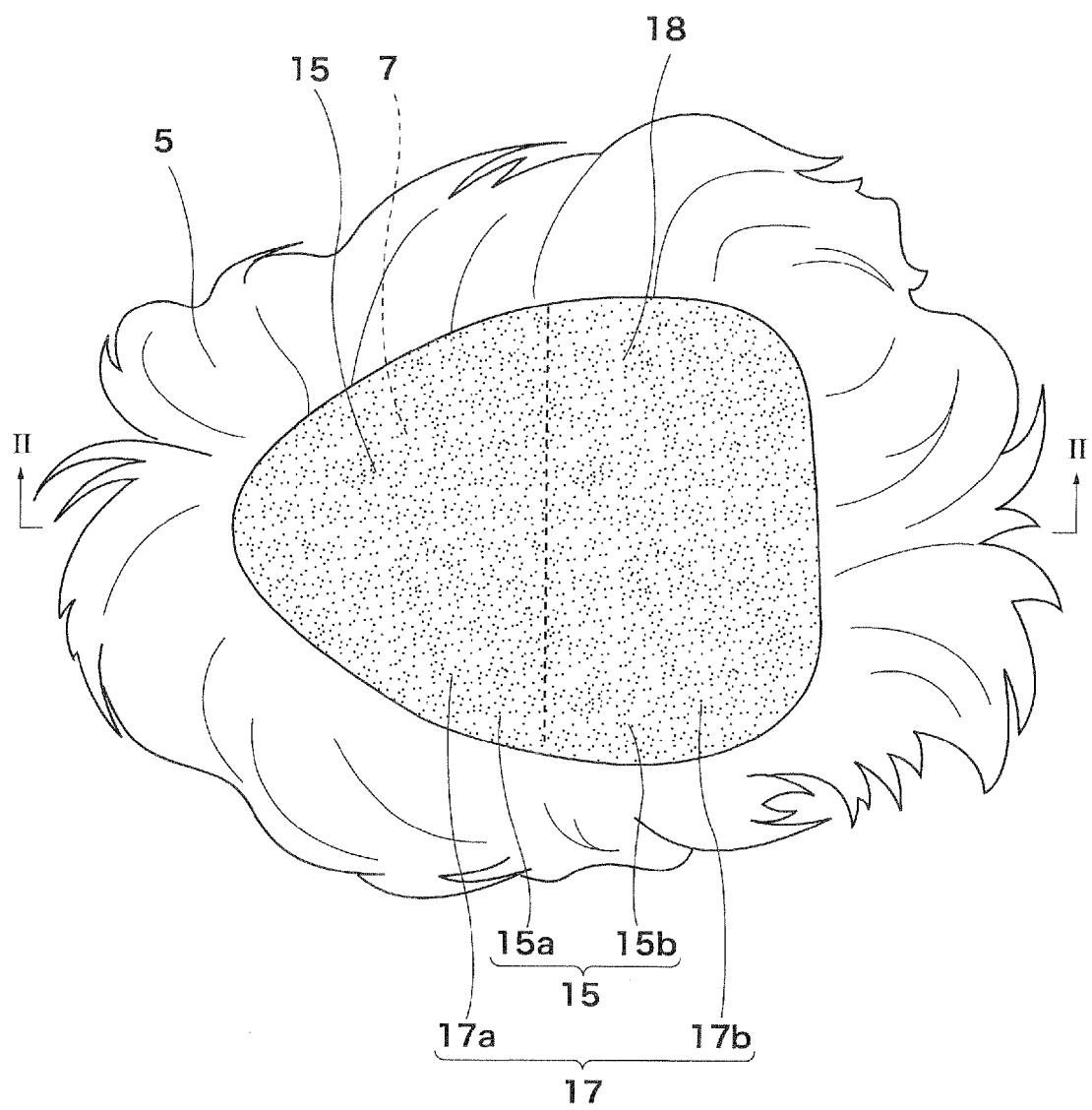
FIG. 1 is a back-side view showing an embodiment of an all-purpose wig according to the present invention.

Next, the all-purpose wig according to the present invention will be described in more detail based on the drawings that illustrate embodiments thereof. As a matter of convenience, any part having the same facility will be represented by the same reference numeral and their explanation will be omitted.

Figure 4:
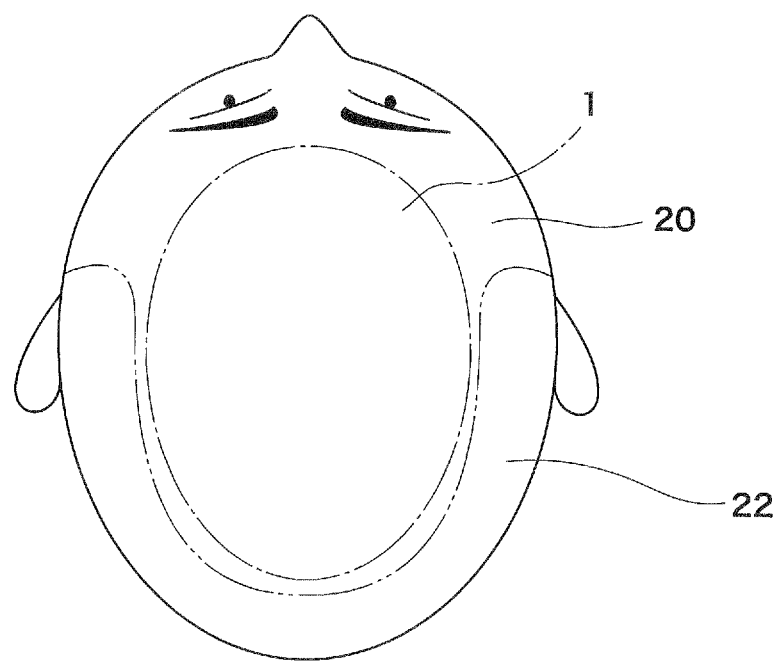
FIG. 4 is a plan view showing the use of the all-purpose wig according to the present invention.

The all-purpose wig 1 according to the present invention comprises a base 3, hair materials 5 implanted to the base 3, an UV curing agent 9 for spot-by-spot securing root portions 7 of the hair materials 5, a first adhesive layer 11 formed with uniform thickness on the entire back surface of the base 3 on which the roots 7 exist, via the UV curing agent 9, a tank layer 13 formed with uniform thickness on the entire back surface of the first adhesive layer 11, a second adhesive layer 15 formed with uniform thickness on the entire back surface of the tank layer 13, for bonding to a skin 20 of a head, a first release layer 17, comprising a release paper, applied peelably to the back surface of the second adhesive layer 15, and a second release layer 18, comprising a release paper, applied peelably to a latter half of the back surface of the first adhesive layer 11. The all-purpose wig 1 is formed as a two-dimensional, multi-layer structure wherein the base, the first adhesive layer 11, the second release layer 18, the tank layer 13, the second adhesive layer 15 and the first release layer 17 are layered in this order. The reference numeral 22 identifies real hairs (as shown in FIG. 4).

The base 3 comprises an ultra-thin and moisture-permeable film-shaped material such as polyurethane. Its thickness $T_1$ is about 30 micrometers, for example. The hair materials 5 comprise polyester fiber, which are implanted such that their root portions 7 that form the implanting base end are adhered closely to one surface of the base 3, with their free end portions being oriented toward the other surface of the base 3. The hair materials 5 are randomly implanted to the base 3. The root portions 7 protrude from the back surface of the base 3 over thickness of one base 3.

Figure 3:
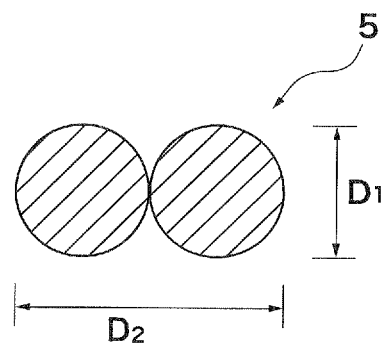
FIG. 3 is a horizontal cross-section of hair materials used in the present invention.

Regarding the diameter of the hair materials 5, as shown in FIG. 3, the diameter $D_1$ is about 0.04-0.05 mm, and the diameter $D_2$ of a pair is about 0.08 mm.

The first adhesive layer 11 comprises adhesive agent including a mixture of silicone and acryl as a main ingredient, having the properties of relatively strong adhesion and relatively large degree of gelling, which is so-called hard-natured adhesive agent. It is formed to have thickness $T_2$ of about 60 micrometers, which is twice the thickness of the base 3. On the contrary, the second adhesive layer 15 comprises adhesive agent including a mixture of silicone and acryl as a main ingredient, having the properties of relatively weak adhesion and relatively small degree of gelling, which is so-called soft-natured adhesive agent. It is formed to have thickness $T_4$ of about 60 micrometers, substantially the same as the first adhesive layer 11.

More specifically, a degree of adhesion (peel adhesion) of the first adhesive layer 11 is on the order of 16.5 N/20 mm, and that of the second adhesive layer 15 is on the order of 3 N/20 mm. These measured values follow JIS Z 0237, Clause 10 (adhesion), which indicate the adhesion to a test plate. However, the adhesion is measured under the above JIS by using a stainless (SUS) plate as the test plate, whereas it is measured according to the present invention with a Bakelite plate as the test plate. The "gelling" means a change of an adhesive component of the adhesive agent to a semi-solid state, which is difficult to be measured even when indexes of JIS Z 0237, Clause 13 (holding power) are referred to. Accordingly, this property is evaluated relatively between the first adhesive layer 11 and the second adhesive layer 15.

The tank layer 13 comprises the same film-shaped material as the base 3 such as polyurethane, having thickness $T_3$ of about 30 micrometers, substantially the same as the base 3, which is laminated between and adjacent to the first adhesive layer 11 and the second adhesive layer 15 to form a sandwich structure.

The first release layer 17 comprises polyethylene terephthalate (PET) and is formed on a surface of the second adhesive layer 15 to be bonded to the skin 20.

The second release layer 18 comprises polyethylene terephthalate (PET), which is layered between the first adhesive layer 11 and the tank layer 13 at latter halves thereof and applied peelably to a latter half of the first adhesive layer 11.

It is said that the stratum corneum 21 of a human skin will replace the old with the new at two-week interval.

The customized wig 2 is prepared by conforming the above-described all-purpose wig 1 to a shape of a head of a specific user, which will be described together with a method for fitting the same, for convenience.

A wig according to the present invention will be effective especially when it is applied to a site having no real hairs, as shown in FIG. 4.

Figure 5:
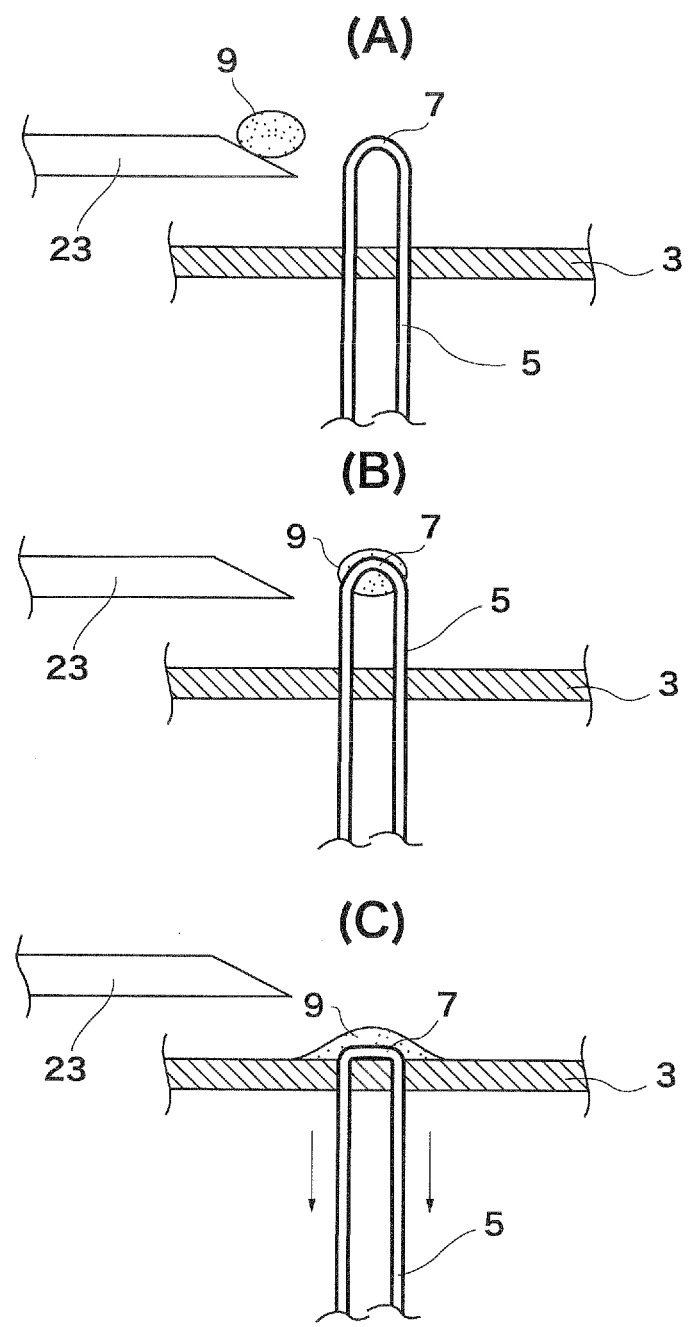
FIG. 5 is an explanatory view showing the operational steps of the all-purpose wig according to the present invention.

Next, a method for production of an all-purpose wig 1 according to the present invention will be described. To the hair materials 5 implanted to the base 3 (FIG. 5(A)), the UV curing agent 9 is applied spot-by-spot by a supply pin 23 (FIG. 5(B). During supply of the UV curing agent 9, the hair materials 5 are stretched so that the root portions 7 are adhered closely to the base 3. By this, substantially all of the UV curing agent 9 will be forced out of the root portion 7, as shown in FIG. 5(C), in which condition the root portion 7 is secured while protruding from the base 3.

Then, the strong adhesive agent is supplied to the entire surface of the base 3 to form the first adhesive layer 11. At this time, as shown in FIG. 2A(B), the root portions 7 still remain protruding from the base 3.

Figure 2A:
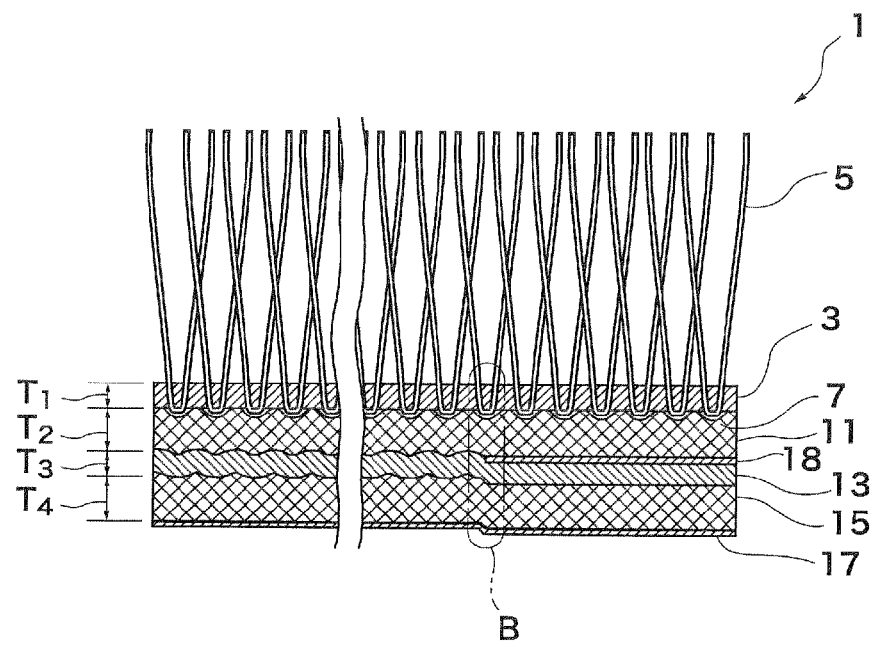
FIG. 2A(A) is an enlarged cross-section showing a part of the all-purpose wig, before customized, according to the present invention, and (B) is an enlarged cross-section of a B part in (A).
Figure 2A:
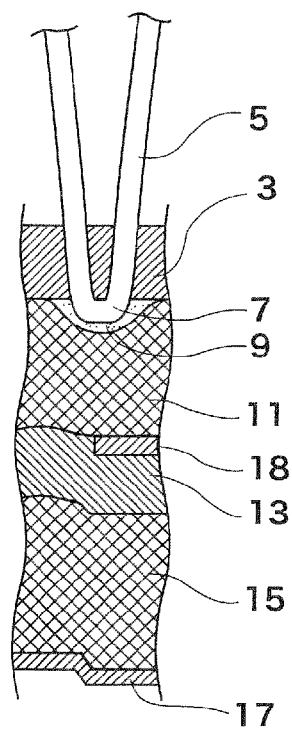

Then, the second release layer 18 is layered on the latter half of the first adhesive layer 11, which is thus bonded to the first adhesive layer 11 (see FIG. 2A(A)).

Then, the tank layer 13 is layered on the entire surfaces of the first adhesive layer 11 and the second release layer 18, which is thus bonded to the first adhesive layer 11 (see FIG. 2A(A)).

Figure 2B:
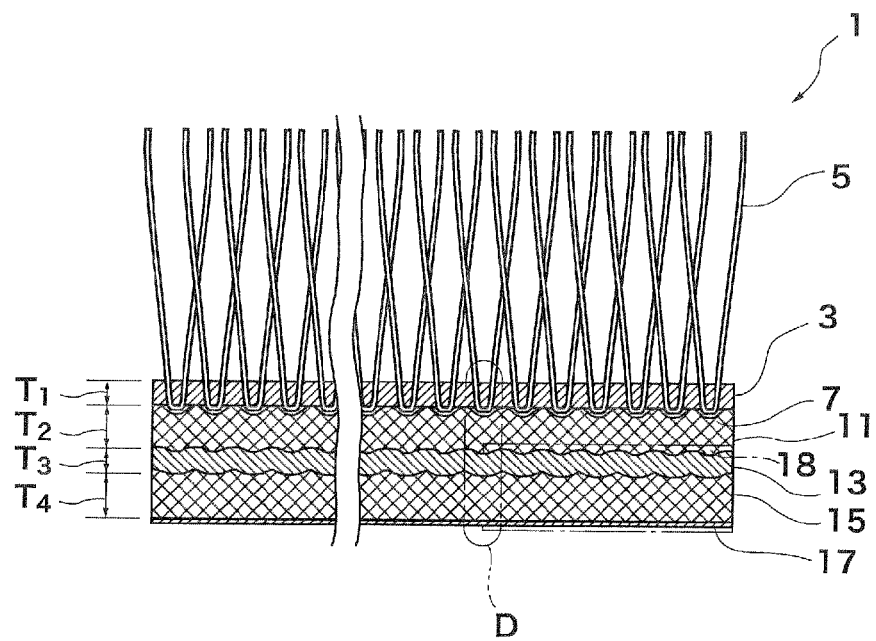
FIG. 2B(C) is an enlarged cross-section of a part of the customized wig after customized, and (D) is an enlarged cross-section of a D part in (C).
Figure 2B:
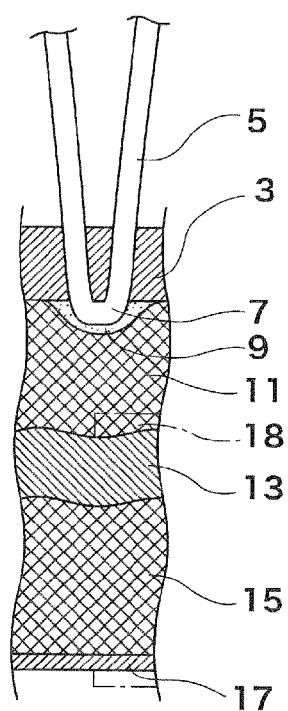

Then, the weak adhesive agent is supplied to the entire surface of the tank layer 13 to form the second adhesive layer 15. At this time, as shown in FIG. 2B(D), the protruding condition of the root portions 7 will substantially disappear by the tank layer 13 and the second adhesive layer 15 that are layered in order onto the outside of the root portions 7, so that the adhesive surface in contact with the skin 20, that is the second adhesive layer 15 will have almost no roughness. At this time, the portion of the second adhesive layer 18 corresponding to the layering portion has got in toward the side of the first release layer 17.

The above-described all-purpose wig 1 is fitted to produce a customized wig that is customized to a specific user, which is carried out by the following steps.

Figure 6:
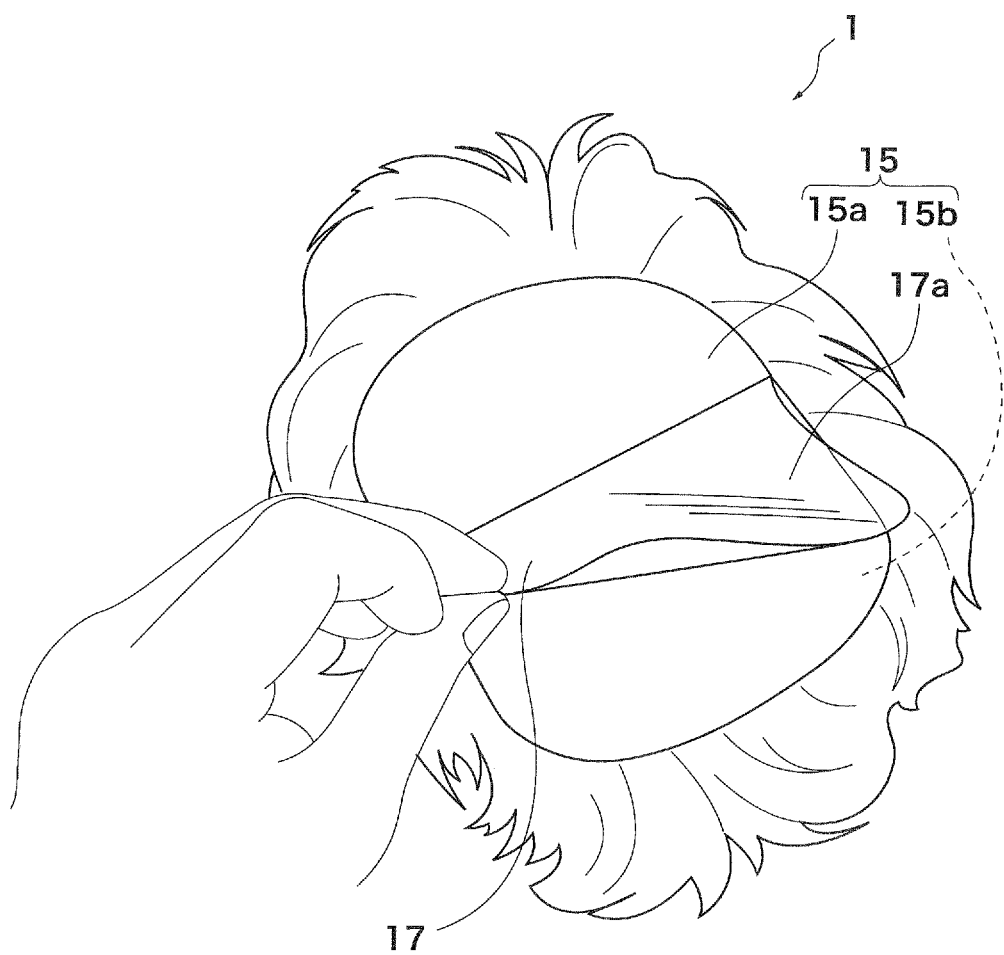
FIG. 6 is a view showing a first step of the fitting process of the all-purpose wig according to the present invention.
Figure 7:
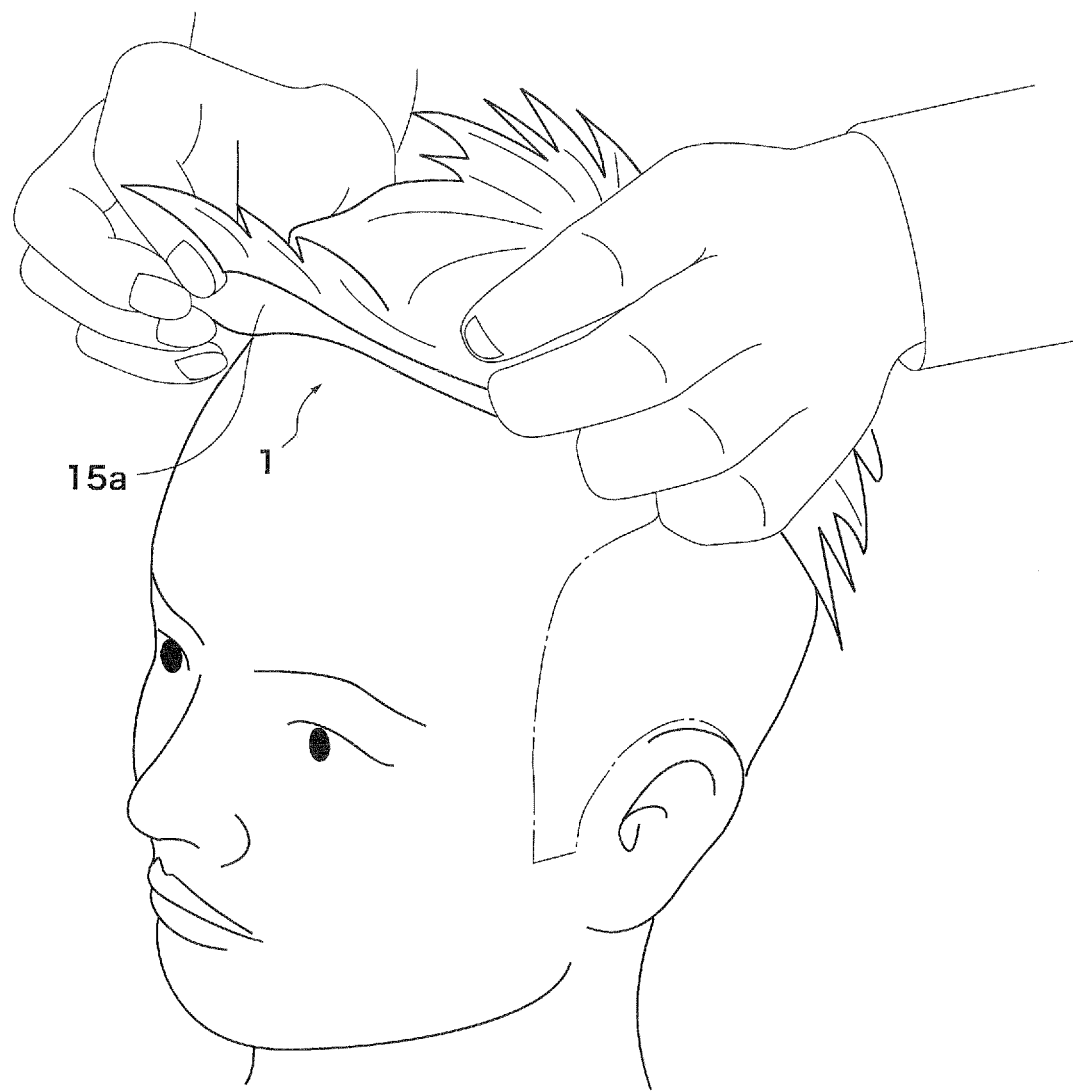
FIG. 7 is a view showing a first step of the fitting process of the all-purpose wig according to the present invention.

First, a former half 17a of the first release paper 17 (that is, a portion of the first release paper 17 that corresponds to a former half portion from the center of the multi-layer structure) is released (FIG. 6), and a former half 15a of the second adhesive layer 15 is applied to a skin 20 of a forehead (First Step, FIG. 7).

Figure 8:
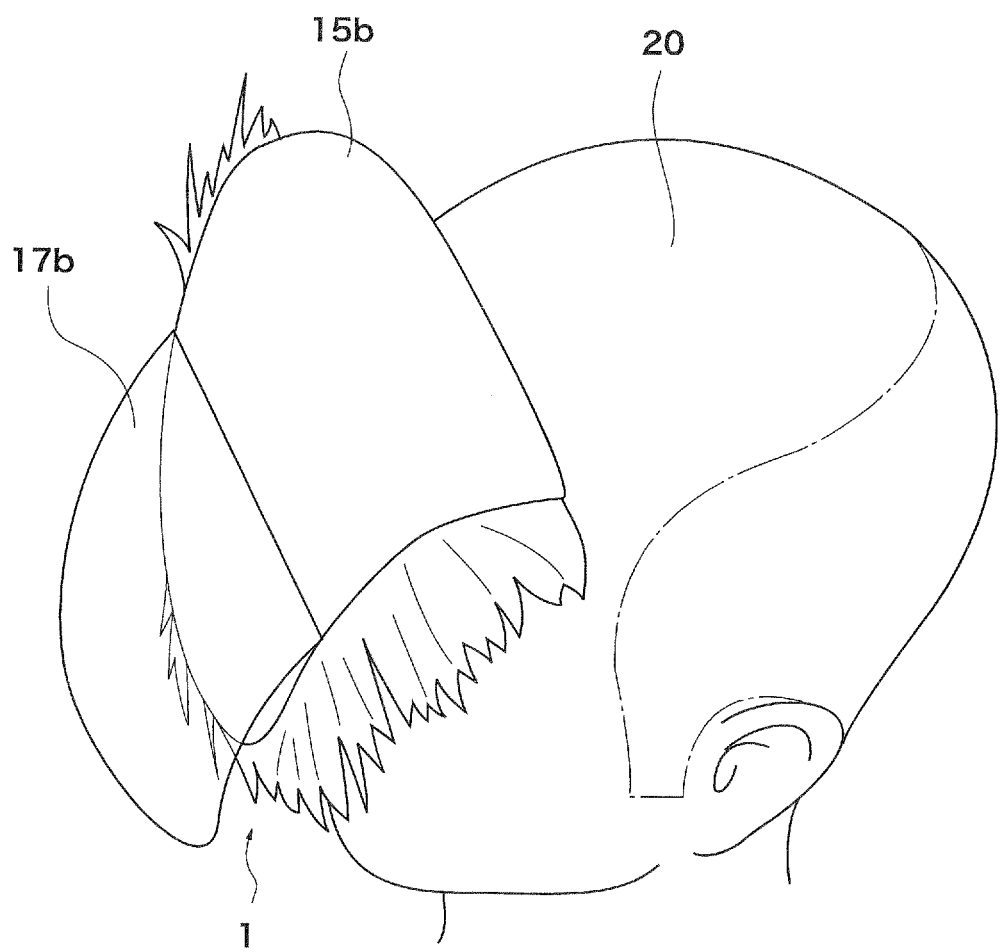
FIG. 8 is a view showing a second step of the fitting process of the all-purpose wig according to the present invention.
Figure 9:
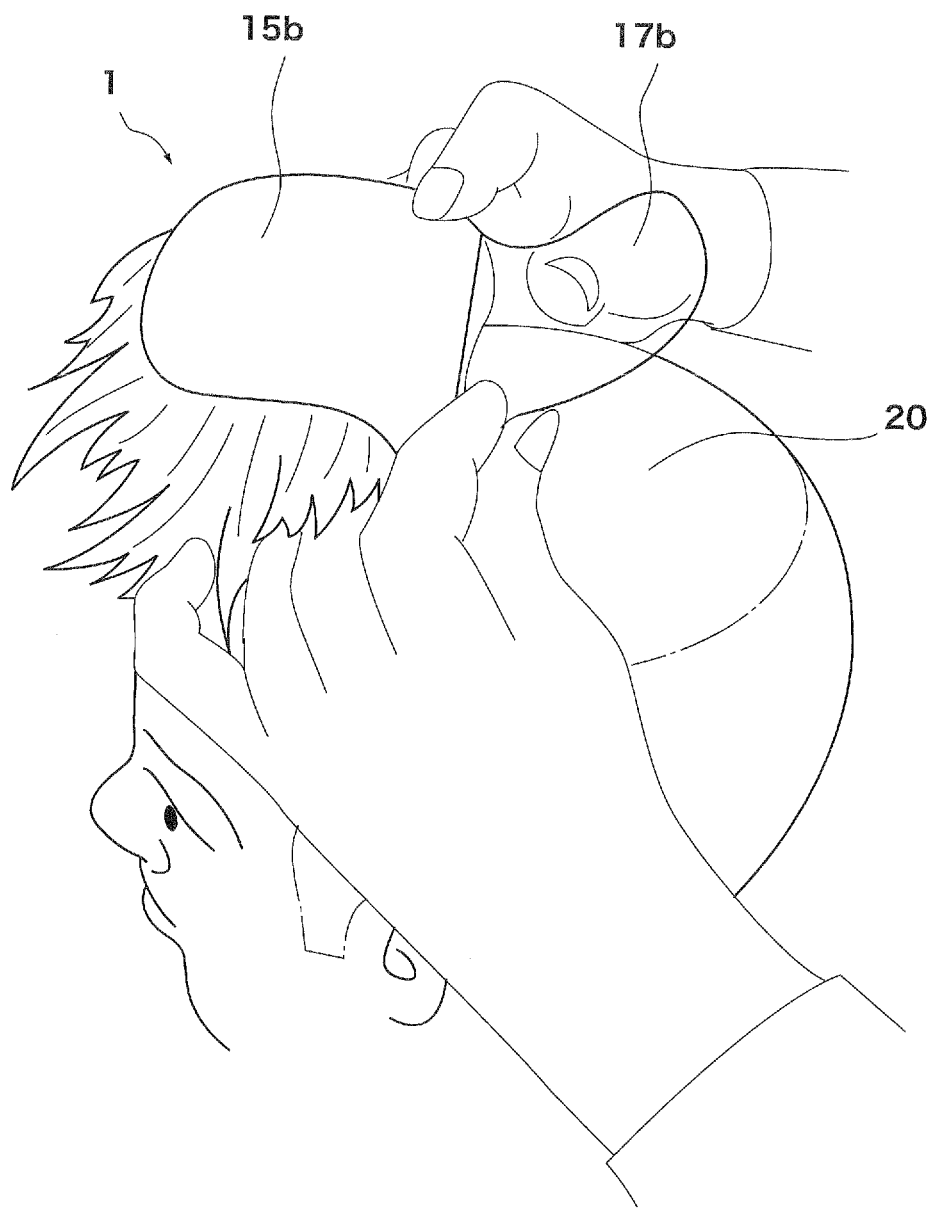
FIG. 9 is a view showing a second step of the fitting process of the all-purpose wig according to the present invention.

Then, a latter half 17b of the first release paper 17 (that is, a portion of the first release paper 17 that corresponds to a latter half portion from the center of the multi-layer structure) is released (FIG. 8), and a latter half 15b of the second adhesive layer 15 is exposed and applied to a skin 20 of a back head (Second Step, FIG. 9).

When applying the latter half 15b of the second adhesive layer 15 to the back head, a first wrinkling step is carried out (Third Step). A numeral 16 denotes a first wrinkle or first wrinkles formed by the first wrinkling step (FIG. 10(A)).

The first wrinkling is carried out to transform the two-dimensional multi-layer structure to a spherical configuration that will generally conform to the shape of a head of a specific user. Because both the tank layer 13 and the second adhesive layer 15 comprise ultra-thin materials, the first wrinkles 16 are formed naturally along the shape of the head, so that the wrinkle(s) may be single or plural. When a plurality of the wrinkles are formed, they may be formed over the entire area of the back head, as shown in FIG. 10(A) and FIG. 11.

Figure 10:
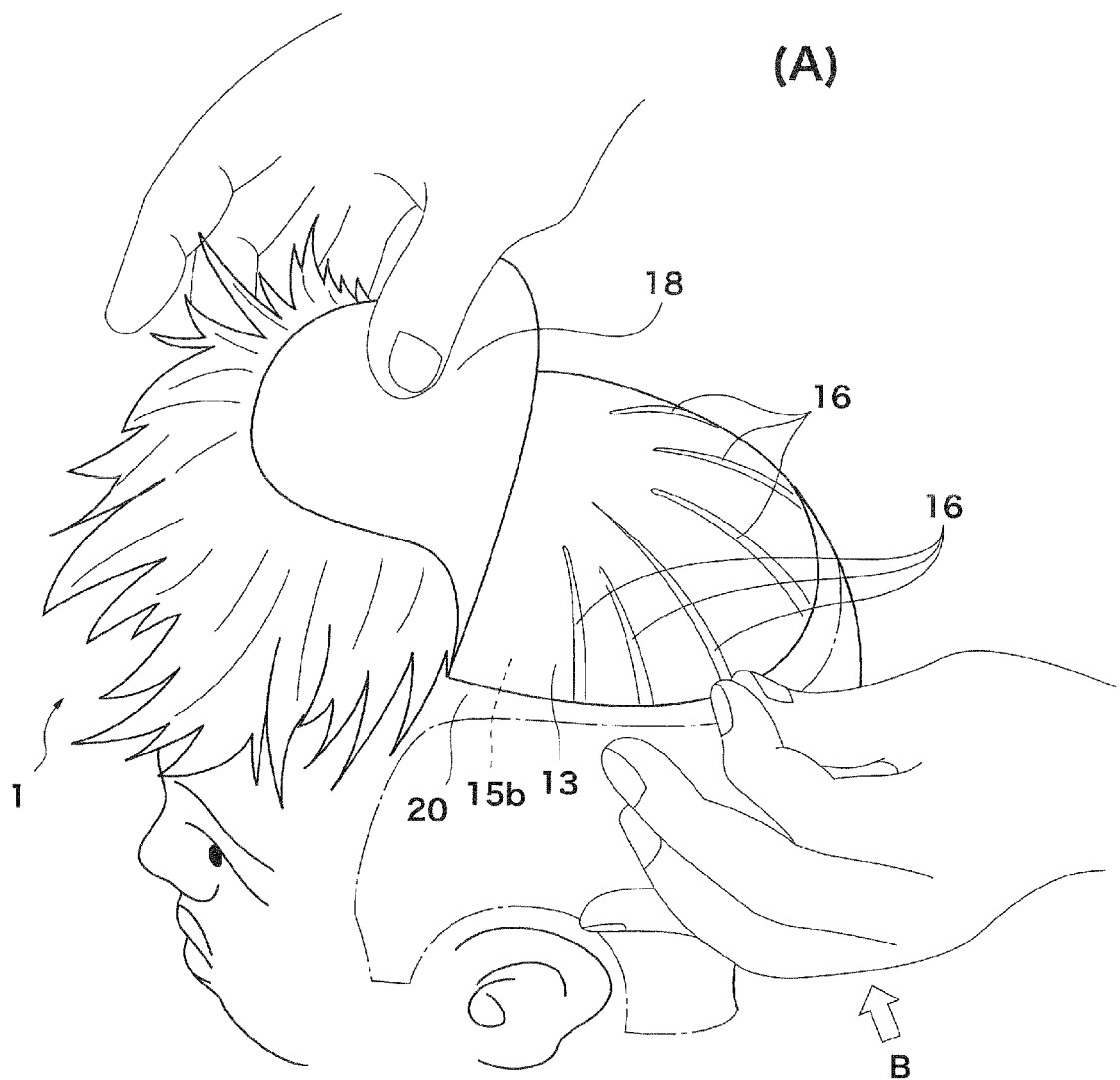
FIG. 10(A) is a view showing a third step of the fitting process of the all-purpose wig according to the present invention. (B) is an enlarged view of (A) when viewed in a B direction.
Figure 10:
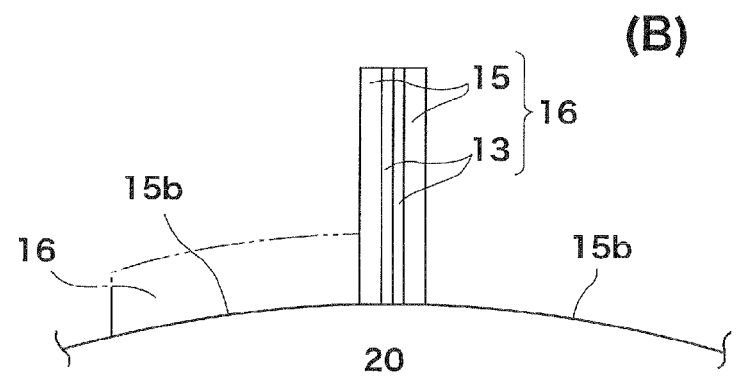
Figure 11:
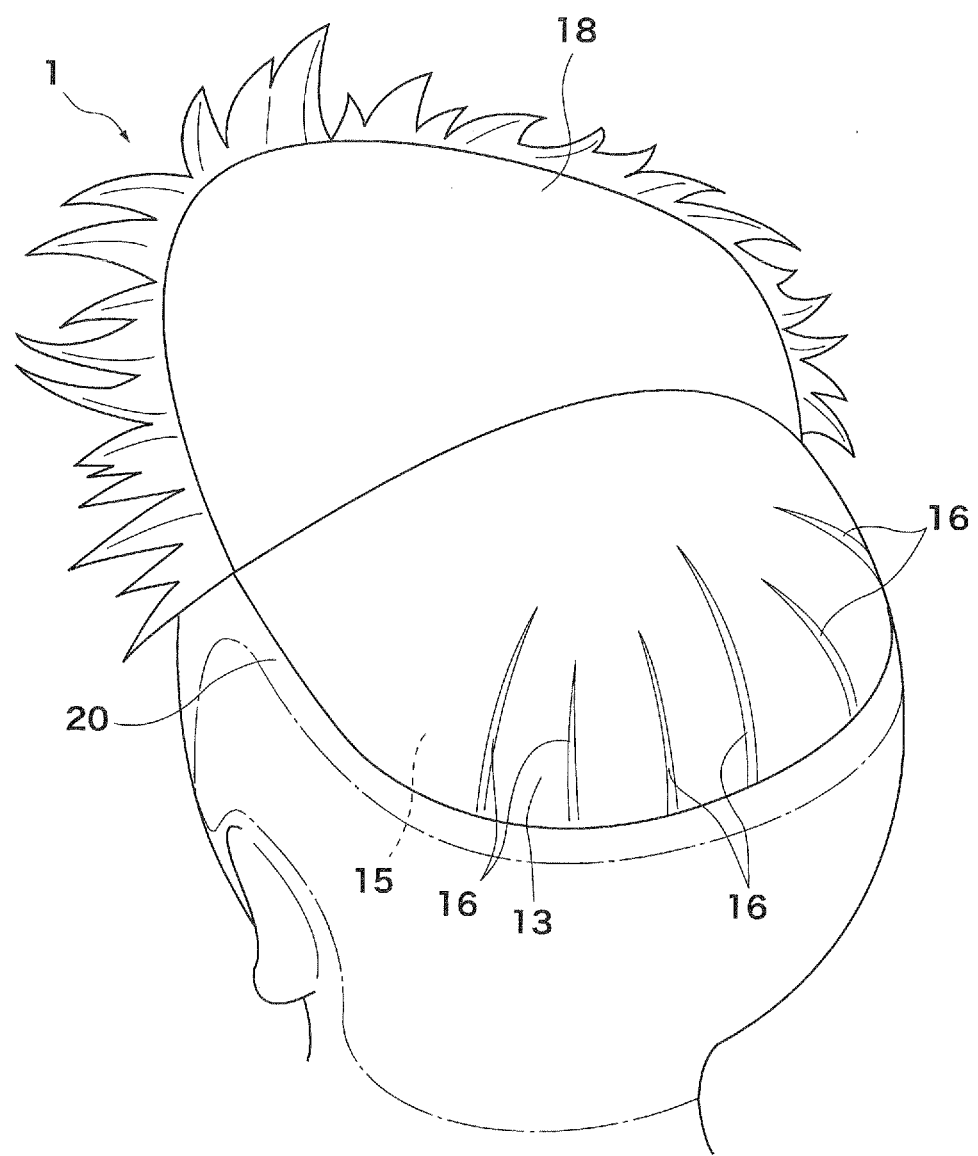
FIG. 11 is a view showing a third step of the fitting process of the all-purpose wig according to the present invention.

As shown in FIG. 10(B), the first wrinkling step comprises raising and gathering a layered body comprising the second adhesive layer 15 and the tank layer 13 at a desired site to be bonded together from the opposite sides to form the first wrinkle 16, laying down the first wrinkle 16 to be bonded to an adjacent portion, and applying the second adhesive layer 15 to a scalp 20 while keeping this condition (FIG. 10(A), (B)). The first wrinkling is carried out at an area where the second release layer 18 exists, that is a back head region in the illustrated example.

Figure 12:
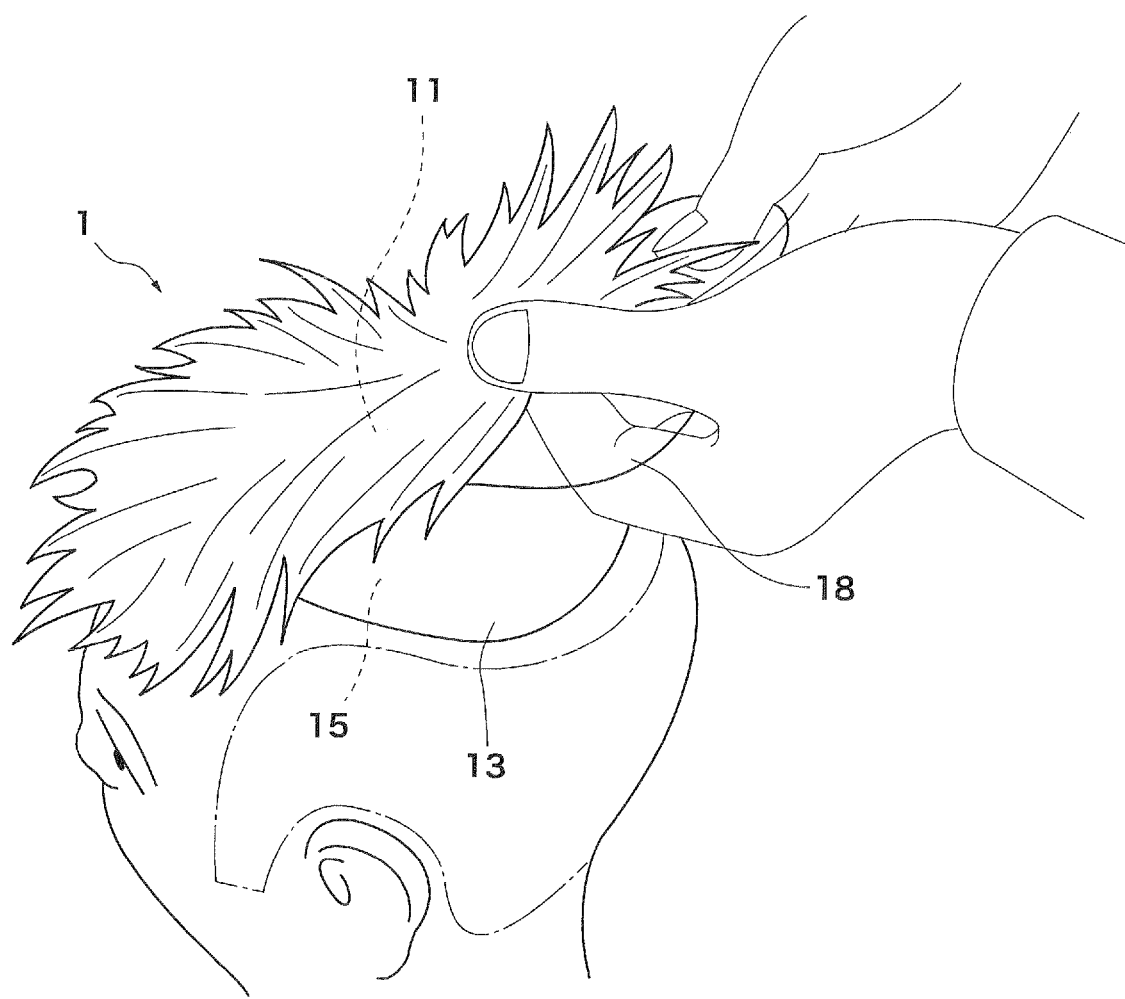
FIG. 12 is a view showing a fourth step of the fitting process of the all-purpose wig according to the present invention.
Figure 13:
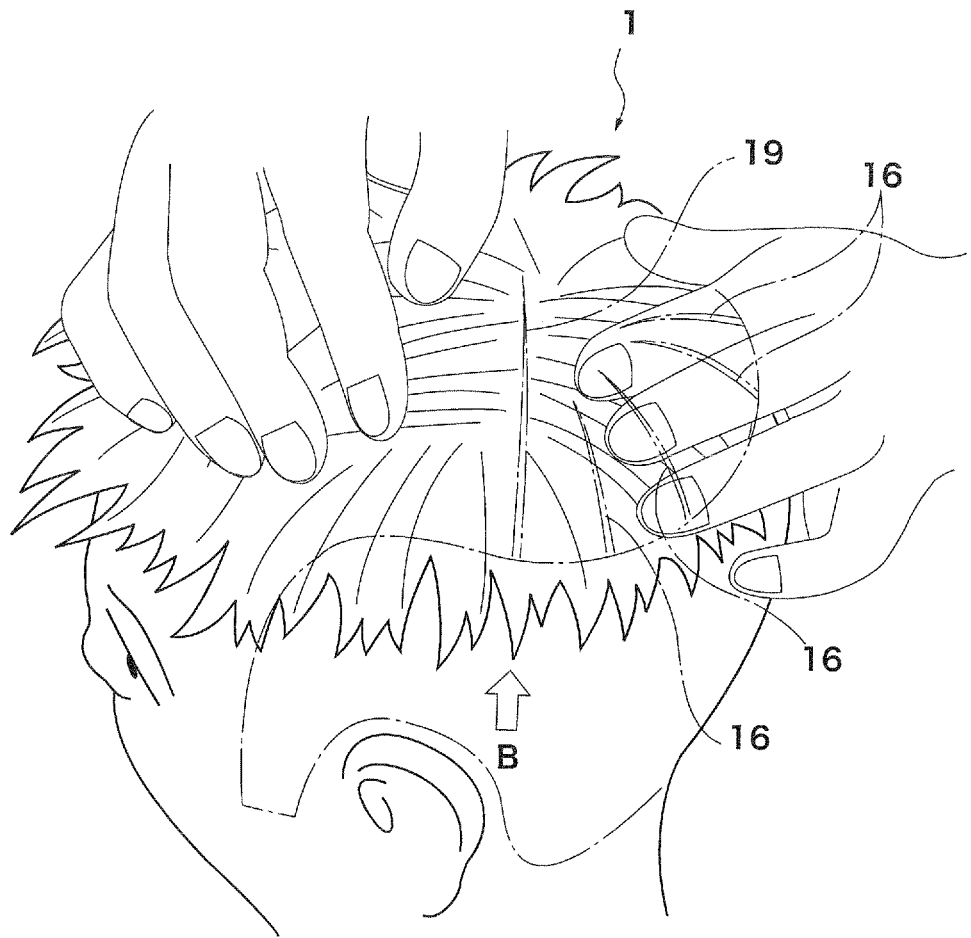
FIG. 13(A) is a view showing fifth and sixth steps of the fitting process of the all-purpose wig according to the present invention. (B) is an enlarged view of (A) when viewed in a B direction.
Figure 13:
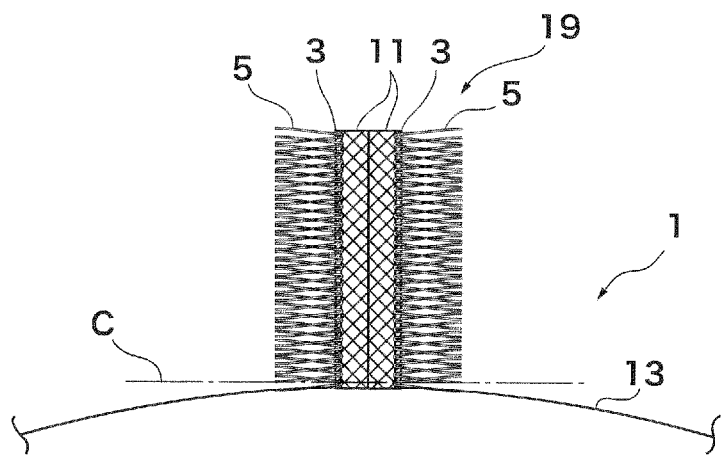

Then, the second release layer 18 is peeled off (FIG. 12). By this, the first adhesive layer 11 becomes exposed (Fourth Step). At this time, the second adhesive layer 15 and the tank layer 13 remain being applied to the head. In this state, "second wrinkling" is carried out (Fifth Step, FIG. 13). The second wrinkling is carried out in order that the multiple-layer construction having a spherical configuration that in general conforms to the head shape of the user becomes more accurately conformable to the head shape of the user. This will make it possible to define an accurate orientation of the hair materials 5 and provide more favorable appearance with more natural feelings.

As shown in FIG. 13(B), the second wrinkling comprises raising and gathering a layered body comprising the first adhesive layer 11 that should be subjected to the wrinkling, said layered body comprising in more detail the first adhesive layer 11 and the base 3 to which the root portion 7, bonded to the first adhesive layer, and the hair materials 5 implanted to the base. The layered body is bonded together from the opposite sides to form a second wrinkle 19.

The number of the second wrinkles 19 may be a single or plural. When a single one is formed, it should be formed preferably at about a center of the occipital region of the head. When plural ones are formed, it should be formed on opposite sides of the occipital region of the head. The second wrinkles should preferably formed at a site different from the first wrinkling portion 16.

Then, the first adhesive layer 11 is applied onto the tank layer 13, while it remains in the secondary wrinkling condition (Sixth Step, see FIG. 13(A)).

Figure 14:
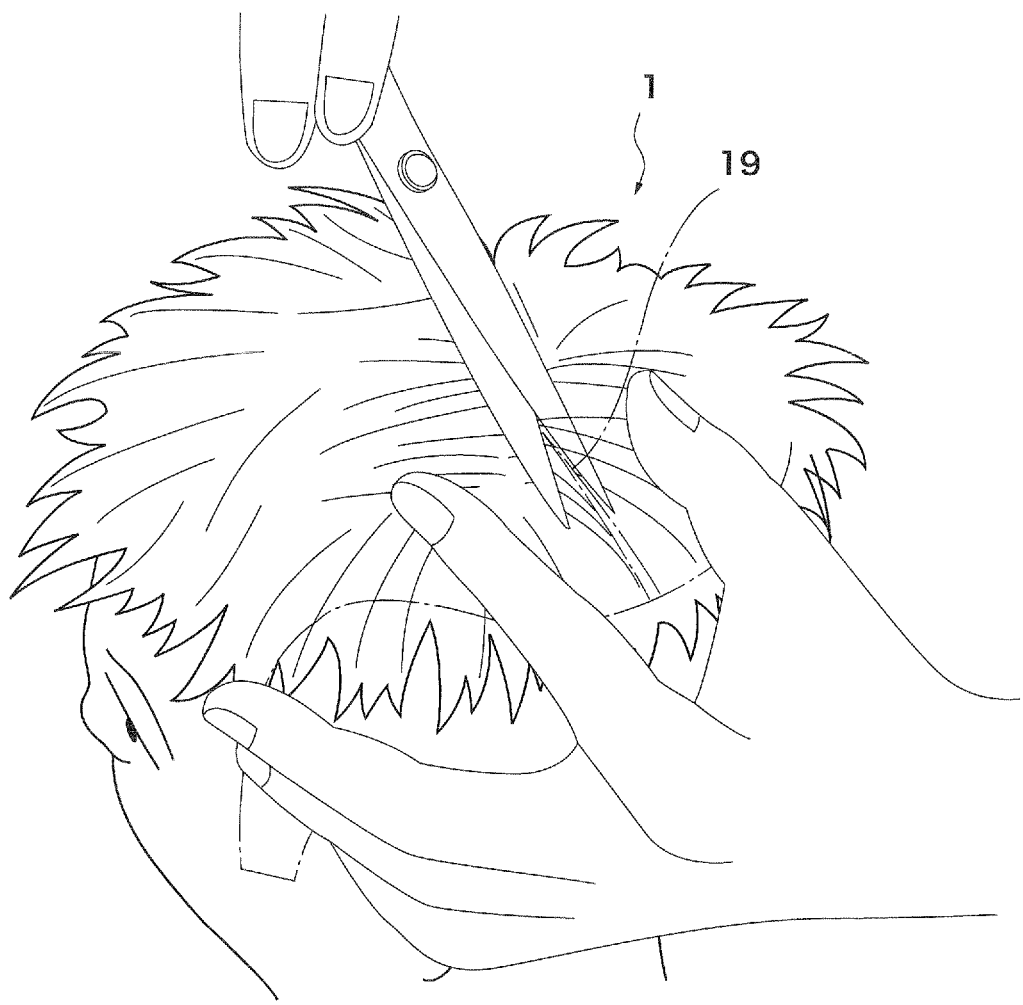
FIG. 14 is a view showing a seventh step of the fitting process of the all-purpose wig according to the present invention.

Then, the second wrinkles 19 comprising the layered body having the first adhesive layer 11, etc. that has been gathered and bonded is cut adjacent at the roots, while the hair materials 5 remain implanted (Seventh Step, FIG. 14). The cut line C is shown in FIG. 13(B).

Thus, the wig has been customized to have a three-dimensional shape that will conform to the head shape of the specific user, resulting in production of a customized wig 2.

The embodiments of the present invention will achieve the following effects and advantages.

<1. Just-Fit Property>

Once the wig according to the above-described embodiment is customized to a shape of a head of a specific user, it is fitted to the head not only by means of adhesion of the second adhesive layer 15, but also due to the multi-layer structure that can be fitted around the head, said physical power being also contributed to fitting. Accordingly, even if the adhesion of the second adhesive layer 15 is relatively weak or becomes somewhat weaker, and even if there are some downy hairs on the surface to which the wig is to be fitted, it can be securely fitted and will be able to prevent accidental removal.

This just-fit property will further weaken the adhesion of the second adhesive layer 15, which may reduce burden to the skin for that.

The wrinkling for customizing the wig to a shape of a head of a specific user is carried out in separate first and second steps, which makes it possible to carry out the customizing operation more accurately and more speedily, due to simplification of the operation.

The just-fit to the head shape of the specific user will prevent noise generation, water entry, dirt entry, etc., greatly improve the sense of use, and improve durability.

<2. Effect of Permeability Etc.>

The wrinkling is carried out in separate first and second steps, wherein the second-wrinkled portion is cut (by the cutting step), by which the surface of the multi-layer structure has no protrusion of unnecessary portions. Accordingly, the base film is prevented from "twisting", which may otherwise appear due to the wrinkling, thereby providing an extremely favorable light permeability to the base 3. As a result, it becomes difficult to distinguish between the human skin and the film base 3, which will provide more natural appearance and feeling.

Because the surface of the multi-layer structure has no protrusion of unnecessary portions, the orientation of the hair materials 5 is not disturbed by wrinkles and remains unchanged and constant, which will further improve the appearance.

The wrinkles that has been subjected to the wrinkling operation is cut so that the hair materials do not protrude, enabling production of a short-hair wig, which cannot be done when there are wrinkles. Furthermore, there is no limitation to specific hairstyles so that the wig may have wider variations.

<3. Handling>

Figure 15:
FIG. 15 is a view for use in explanation of the effects of the customized wig according to the present invention, which is an oblique view viewed from the front.
Figure 16:
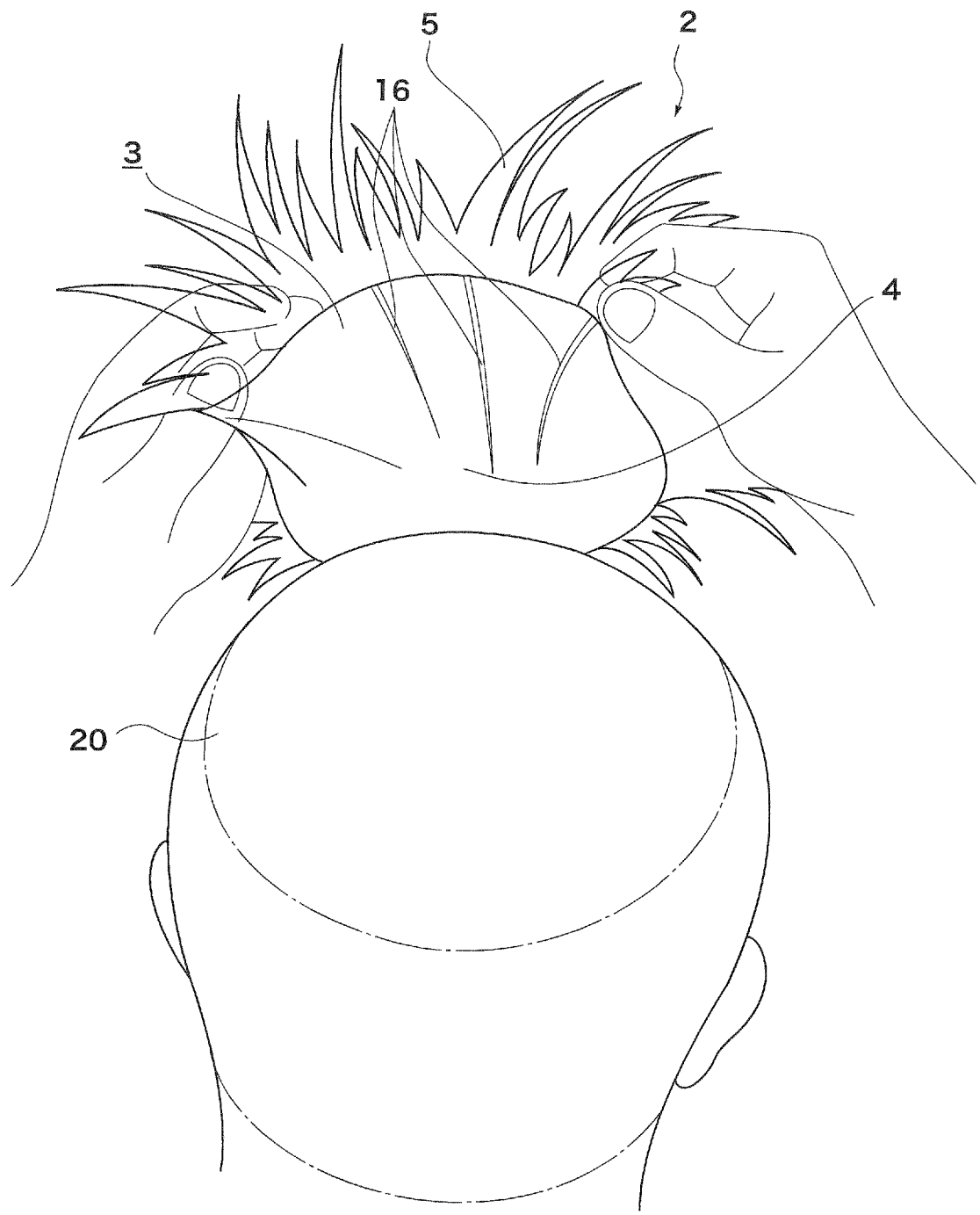
FIG. 16 is a view for use in explanation of the effects of the customized wig according to the present invention, which is an oblique view viewed from the rear.

The fitting of the wig at the second and succeeding time, that is the fitting of a customized wig 2 is carried out as shown in FIG. 15 and FIG. 16 in such a manner that a central portion 4 of the multi-layer structure of the wig having a three-dimensional configuration is convexed downwardly. Therefore, the surface to be bonded to the skin can be confirmed with eyes, which achieves very easy fitting.

In addition, since the central portion 4 of the multi-layer structure is convexed downwardly, the hair materials 5 are moved upwardly, by which the hair materials 5 may be prevented from being dragged into between the wig and the skin at the time when the wig is to be fitted.

Accordingly, the wig may be easily and speedily fitted, thereby improving the handling property.

<4. Adaptability>

When the prior wig is customized to conform with a head shape of a user, it must involve a patterning step, a base producing step, a hair implanting step, etc, which requires about 40 days at the soonest. However, in accordance with a wig according to the present invention, an all-purpose wig having a two-dimensional configuration that is conformable to any user is manufactured in advance, which may be individually customized to a head shape of a specific user, even in a day.

Accordingly, it contributes to a quick delivery and a great cost reduction.

<5. Adhesion Holding Power by Planar Bonding>

First, the second adhesive layer 15 has substantially a flat surface due to the presence of the tank layer 13 (see FIG. 2B(C)). In addition, the tank layer 13 comprising moisture-permeable material will absorb sweat and so on generated while it is fitted to the skin 20, which further reduces the protuberance by the root portions.

As a consequence, the second adhesive layer 15 may be bonded to the skin 20 plane-by-plane, so that the adhesion will preserve for a long period of time, in spite of the weak adhesive agent.

Regarding this point, if a moisture content in sweat should be transferred into the second adhesive layer 15, the molecular structure of the adhesive agent is destroyed so that the gelling component in the second adhesive layer 15 will easily be gelated, which excessively strengthens the adhesion. In contrast, according to the embodiment of the present invention, because such transfer of gelation may be interrupted by the tank layer 13 positioned between the second adhesive layer 15 and the first adhesive layer 11, which, therefore, maintains the weak adhesion for a long period of time.

Figure 17:
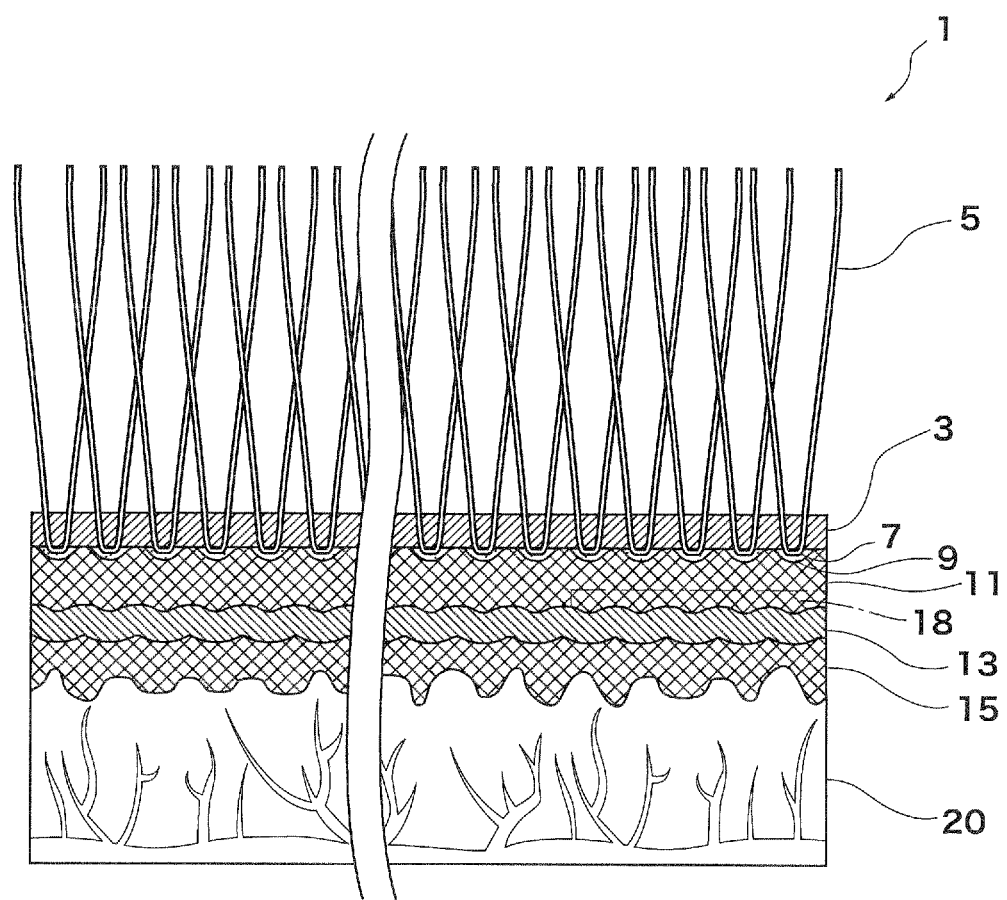
FIG. 17 is a summarized, enlarged cross-section of a skin, for use in explanation of the effects of the all-purpose wig according to the present invention.

Although, as shown in FIG. 17, the skin 20 has slight unevenness in a microscopic viewpoint, because the above-described surface to be subjected to planar contact is the ultra-thin, multi-layer structure, the adhesion surface may be tightly fitted to conform with the unevenness of the skin 20. Accordingly, it may be bonded to the entire surface of the skin 20 to which the skin is to be fitted.

Figure 18:
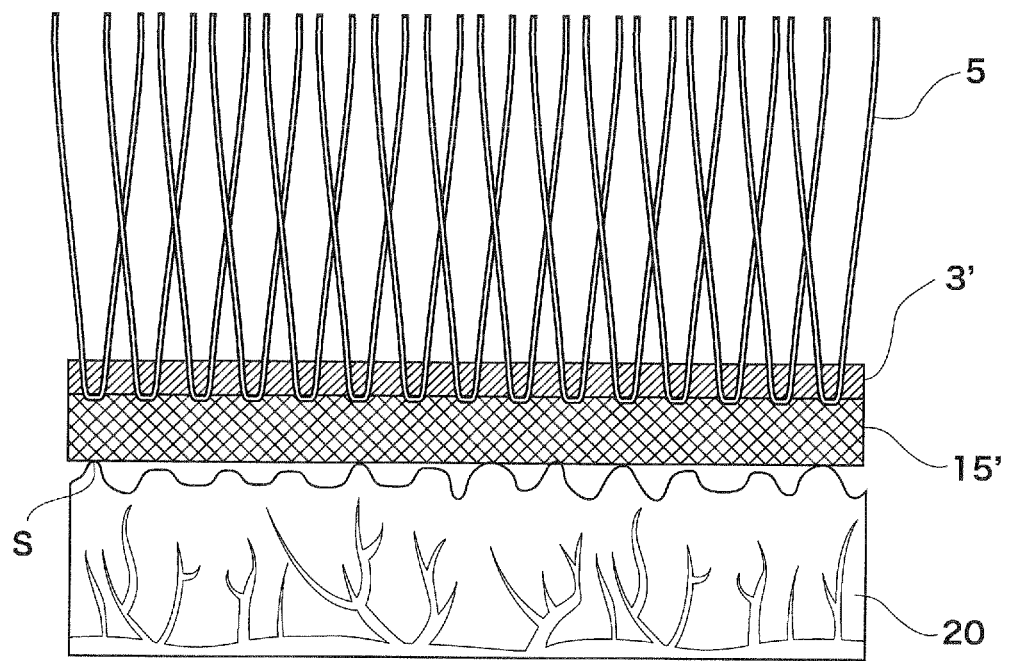
FIG. 18 is a summarized, enlarged cross-section showing a comparable example to FIG. 17.
Figure 21:
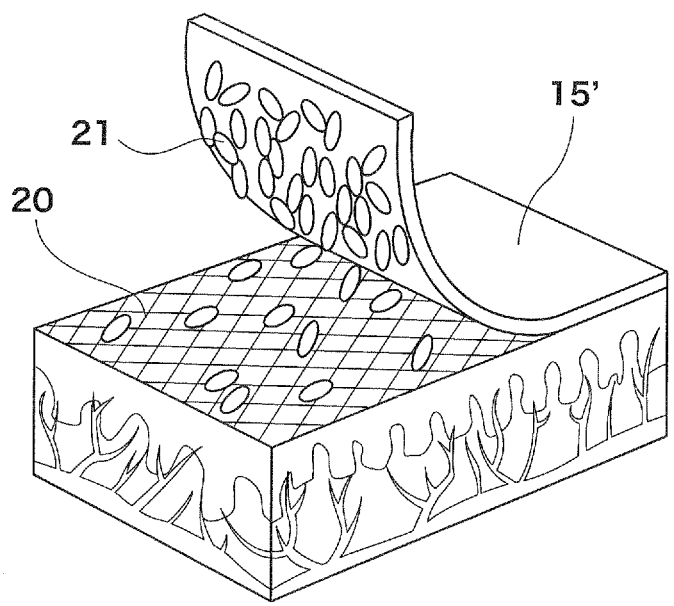
FIG. 21 is a summarized cross-section showing a part of the skin, for use in explanation of the prior all-purpose wig.

Consequently, even if the adhesion of the adhesive agent that is bonded to the skin 20 is relatively weak, it is bonded to the entire surface of the skin 20, thereby maintaining the adhesion holding force and preventing accidental removal. Regarding this point, if the adhesive layer 15' is bonded to the skin 20 only at points S, the adhesion holding force cannot be maintained, as shown in FIG. 18. Accordingly, the adhesive layer 15' should comprise adhesive agent having relatively strong and stiff properties as in the prior art, otherwise it could be accidentally removed. However, when the adhesive layer 15' comprises adhesive agent having relatively strong and stiff properties, a considerable number of stratum corneum 21 should be separated from the skin 20, as shown in FIG. 21.

The presence of moisture content such as sweat will degrade the adhesion. However, since the sweat, etc. entering the second adhesive layer 15 may be absorbed into the tank layer 13, so that the second adhesive layer 15 has less influence by the sweat and other moisture content and, therefore, maintains its adhesion. This will also contribute to the fact that the second adhesive layer 15 may be kept bonded to the skin 20, nevertheless it has relatively weak adhesion.

Figure 19:
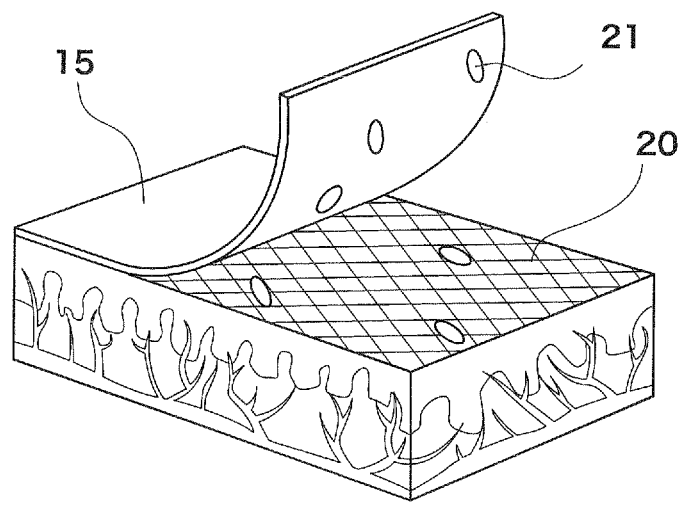
FIG. 19 is a summarized, enlarged cross-sectional oblique view showing a part of the skin, for use in explanation of the effects of the all-purpose wig according to the present invention.
Figure 20:
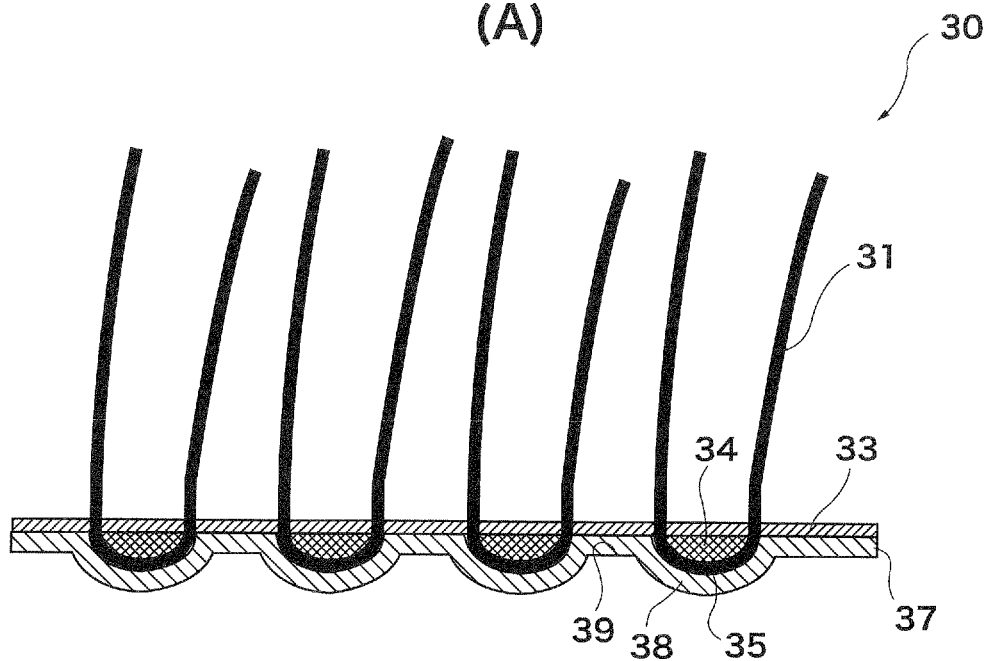
FIG. 20(A) is an enlarged cross-section showing a part of a prior disposable wig, and (B) is an enlarged cross-section showing the part that has been turned reversal when in use.
Figure 20:
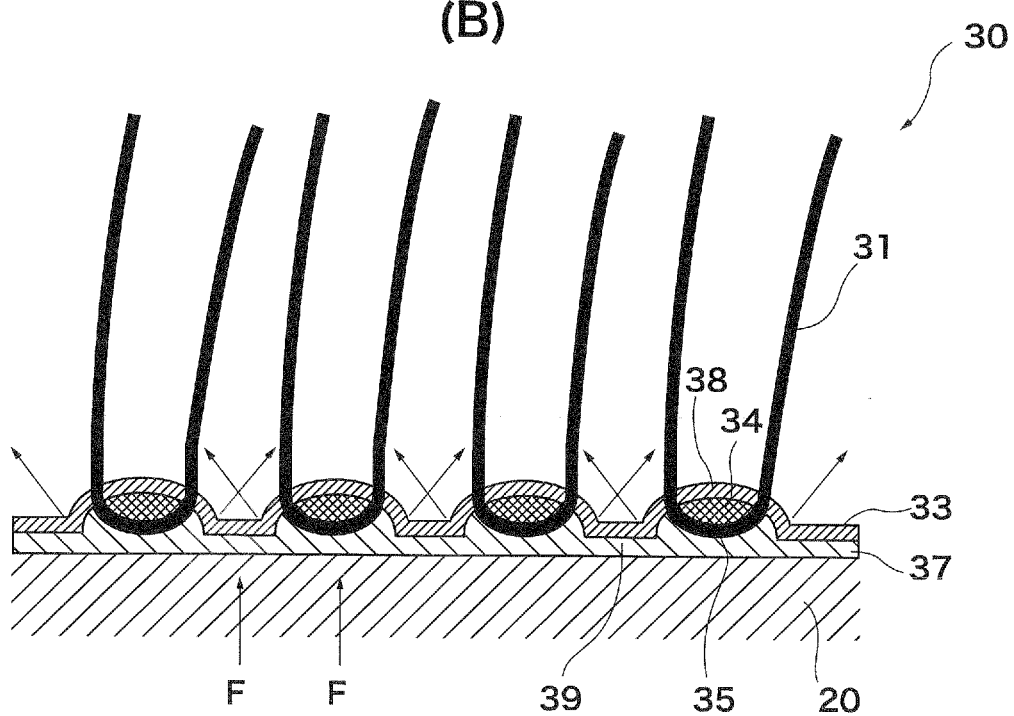

Because the adhesion of the second adhesive layer 15 to the skin 20 is relatively weak, when detaching the wig, the stratum corneum 21 of the skin 20 would rarely be separated, as shown in FIG. 19.

Further, because the adhesion of the second adhesive layer 15 is relatively weak, if the stratum corneum 21 should be attached to the layer surface, it is easy to be removed by washing with water. This will activate the adhesive surface and enable repeated use (about 30 times, for example).

<6. Easy Handling>

The hair materials 5 implanted onto the base 3 will act as core in a sense. In addition, the first adhesive layer 11 is laminated and bonded between the base 3 to which the hair materials 5 are implanted and the tank layer 13 comprising the same film-shaped material as the base 3 to form a sandwich structure. This will restrict the tendency of the first adhesive layer 11 to shrink the base 3 due to its relatively strong adhesion, thereby preventing the base 3 from crumpling.

Since the tank layer 13 comprises the same film-shaped material as the base 3, it provides a good balance with respect to the adhesive agent. This will also prevent the base 3 from excessively shrinking and prevent lowering of hygroscopic property.

Because the base 3 does not shrink, the wig may easily be handled when fitted by the user. Further, even if a tension is applied to the base 3 when the wig is detached, its excessive stretch is restricted, which provides easy handling.

<7. Easy Remake>

The all-purpose wig 1 may be reused by periodically exchanging the second adhesive layer 15 until the base 3 or the hair materials 5 has been used up. When it is remake, the second adhesive layer 15 is removed.

Removal of the second adhesive layer 15 may be done by physical removal, that is scraping, for example. At this removal, the surface of the second adhesive layer 15 is prevented from transforming three-dimensionally or shrinking, due to the above-described core function of the hair materials 5 and the multi-layered structure.

Consequently, the second adhesive layer 15 is easy to be removed. It may be remade, even easily.

<4. Other Effects>

Because the tank layer 13 comprises the same film-shaped material as the base 3 and has the same thickness as the base 3, it provides further improved light-permeability when fitted to the skin 20. Accordingly, there is an effect of preventing the shining of the base 3, which makes it more difficult to be identified as a wig. Regarding this point, if the tank layer 13 should comprise different material rather than the base 3 or if it is excessively thick, the light-permeability becomes unbalanced, which would make it easier to be identified as a wig.

The present invention is not limited to the above-described embodiments. For example, the location site (layering portion) of the second release layer 18 is optional, which may be formed on a former half of the first adhesive layer 11. The thickness of the base 3 and the tank layer 13 may be thinner than in the above-described embodiment, which may be ultra-thin such as about 10 micrometers and 20 micrometers, for example. The diameter of the hair materials 5 mentioned in the above-described embodiments should be understood as one example. The application site is not limited to the head, as far as it is a human skin.

INDUSTRIAL APPLICABILITY

The all-purpose wig, the method for fitting the wig and the customized wig according to the present invention is applicable to a wig for a head, for example.

EXPLANATION OF REFERENCE NUMERALS

1 All-purpose wig
2 Customized wig
3 Base
4 Central portion
5 Hair material
7 Root portion
9 UV curing agent
11 First adhesive layer
13 Tank layer
15 Second adhesive layer
16 First wrinkle
17 First release layer
18 Second release layer
19 Second wrinkle
20 Skin
21 Stratum corneum
22 Real hair
23 Supply pin

The invention claimed is:

1. An all-purpose wig comprising:
a base,
hair materials implanted to the base,
a first adhesive layer formed on an entire surface of the base at a side of root portions of said hair materials,
a tank layer,
a second adhesive layer to be bonded to a skin,
a first release layer, and
a second release layer;
wherein:
said base comprises an ultra-thin and moisture permeable film-shaped material;
said hair materials are implanted such that their root portions that form the implanting base end are adhered closely to one surface of said base, with their free end portions being oriented toward the other surface of said base;
said first adhesive layer comprises an adhesive agent having the properties of relatively strong adhesion and relatively large degree of gelling;
said second adhesive layer comprises an adhesive agent having the properties of relatively weak adhesion and relatively small degree of gelling;
said tank layer comprises the same film-shaped material as said base;
said first adhesive layer and said second adhesive layer are provided adjacent to each other with said tank layer therebetween;
said first release layer is applied peelably to the entire surface of said second adhesive layer on a side that is fit to the skin;
said second release layer is layered partially between said first adhesive layer and said tank layer and applied peelably to said first adhesive layer; and
said wig is formed as a substantially two-dimensional, multi-layer structure wherein said base, said first adhesive layer, said second release layer, said tank layer, said second adhesive layer and said first release layer are laminated in this order.

2. The all-purpose wig according to claim 1, wherein said second release layer is formed at a latter half of said first adhesive layer.

3. The all-purpose wig according to claim 2, wherein said hair materials are implanted onto said base while their free end portions are in stretched condition.

4. The all-purpose wig according to claim 1, wherein said hair materials are implanted onto said base while their free end portions are in stretched condition.

5. The all-purpose wig according to claim 1, wherein the adhesion of said first adhesive layer is on the order of five times of the adhesion of said second adhesive layer.

6. The all-purpose wig according to claim 1, wherein said hair materials are randomly implanted onto said base.

7. A customized wig comprising:
base,
hair materials implanted to the base,
a first adhesive layer formed on an entire surface of the base at a side of root portions of said hair materials,
a tank layer,
a second adhesive layer to be bonded to a skin, a first release layer and a second release layer;
wherein:
said base comprises an ultra-thin and moisture permeable film-shaped material;
said hair materials are implanted such that their root portions that form the implanting base end are adhered closely to one surface of said base, with their free end portions being oriented toward the other surface of said base;

said first adhesive layer comprises an adhesive agent having the properties of relatively strong adhesion and relatively large degree of gelling;

said second adhesive layer comprises an adhesive agent having the properties of relatively weak adhesion and relatively small degree of gelling;

said tank layer comprises the same film-shaped material as said base;

said first adhesive layer and said second adhesive layer are provided adjacent to each other with said tank layer therebetween;

said first release layer is applied peelably to the entire surface of said second adhesive layer on a side that is fit to the skin;

said second release layer is layered partially between said first adhesive layer and said tank layer and applied peelably to said first adhesive layer; and said wig is formed as a substantially three-dimensional, multi-layer structure comprising said base, said first adhesive layer, said second release layer, said tank layer, said second adhesive layer and said first release layer are laminated in this order, wherein said tank layer is given first wrinkles by a first wrinkling step, said first wrinkles being bonded to adjacent portions, and said first adhesive layer is given second wrinkles by a second wrinkling step, said second wrinkles being cut adjacent at their roots.

8. The customized wig according to claim 7, wherein said second release layer is formed at a latter half of said first adhesive layer.

9. The customized wig according to claim 8, wherein said hair materials are implanted onto said base while their free end portions are in stretched condition.

10. The customized wig according to claim 7, wherein said hair materials are implanted onto said base while their free end portions are in stretched condition.

11. The customized wig according to claim 7, wherein the adhesion of said first adhesive layer is on the order of five times of the adhesion of said second adhesive layer.

12. The customized wig according to claim 7, wherein said hair materials are randomly implanted onto said base.

\* \* \* \* \*